United States Patent [19]

Eifler et al.

[11] 3,931,320

[45] Jan. 6, 1976

[54] PROCESS FOR THE PRODUCTION OF AROMATIC POLYAMINES

[75] Inventors: Willi Eifler, Schildgen; Roderich Raue, Leverkusen-Wiesdorf; Ernst-Heinrich Rohe, Leverkusen; Josef Finkel, Cologne-Stammheim, all of Germany

[73] Assignee: Bayer Aktiengesellschaft, Leverkusen Bayerwerk, Germany

[22] Filed: May 23, 1972

[21] Appl. No.: 256,036

[30] Foreign Application Priority Data
June 2, 1971 Germany............................ 2127263

[52] U.S. Cl.. 260/570 D; 260/2.5 AT; 260/453 AM
[51] Int. Cl............................................... C07c 87/28
[58] Field of Search................................ 260/570 D

[56] References Cited
UNITED STATES PATENTS
3,297,759   1/1967   Curtiss et al...................... 260/570
FOREIGN PATENTS OR APPLICATIONS
1,183,153   3/1970   United Kingdom................. 260/570

*Primary Examiner*—R. V. Hines
*Attorney, Agent, or Firm*—Joseph C. Gil

[57] ABSTRACT

A process for the production of aromatic polyamines comprising condensing primary or secondary aromatic amines with formaldehyde or a formaldehyde precursor in the presence of an acid catalyst and liberating the polyamines on completion of condensation by the addition of a basically reacting reagent, wherein a mixture containing amine, catalyst, aldehyde, precondensates formed therefrom, and water, issuing from a mixer at a maximum temperature of about 40°C., is separated into a. a side stream in which the heat liberated from the reacting mixture is dissipated in a heat exchanger following dilution of the total quantity of mixture of amine and catalyst, cooled to below about 40°C., required for the reaction and the mixture thus obtained is reintroduced at a temperature of at most about 40°C. into the mixer where formaldehyde is added, and b. a main stream which is pumped, through a reaction zone kept at a maximum of about 40°C., into one or more heated residence reactors arranged in series in which the condensation reaction is completed at from about 80°C. to about 200°C.

5 Claims, 1 Drawing Figure

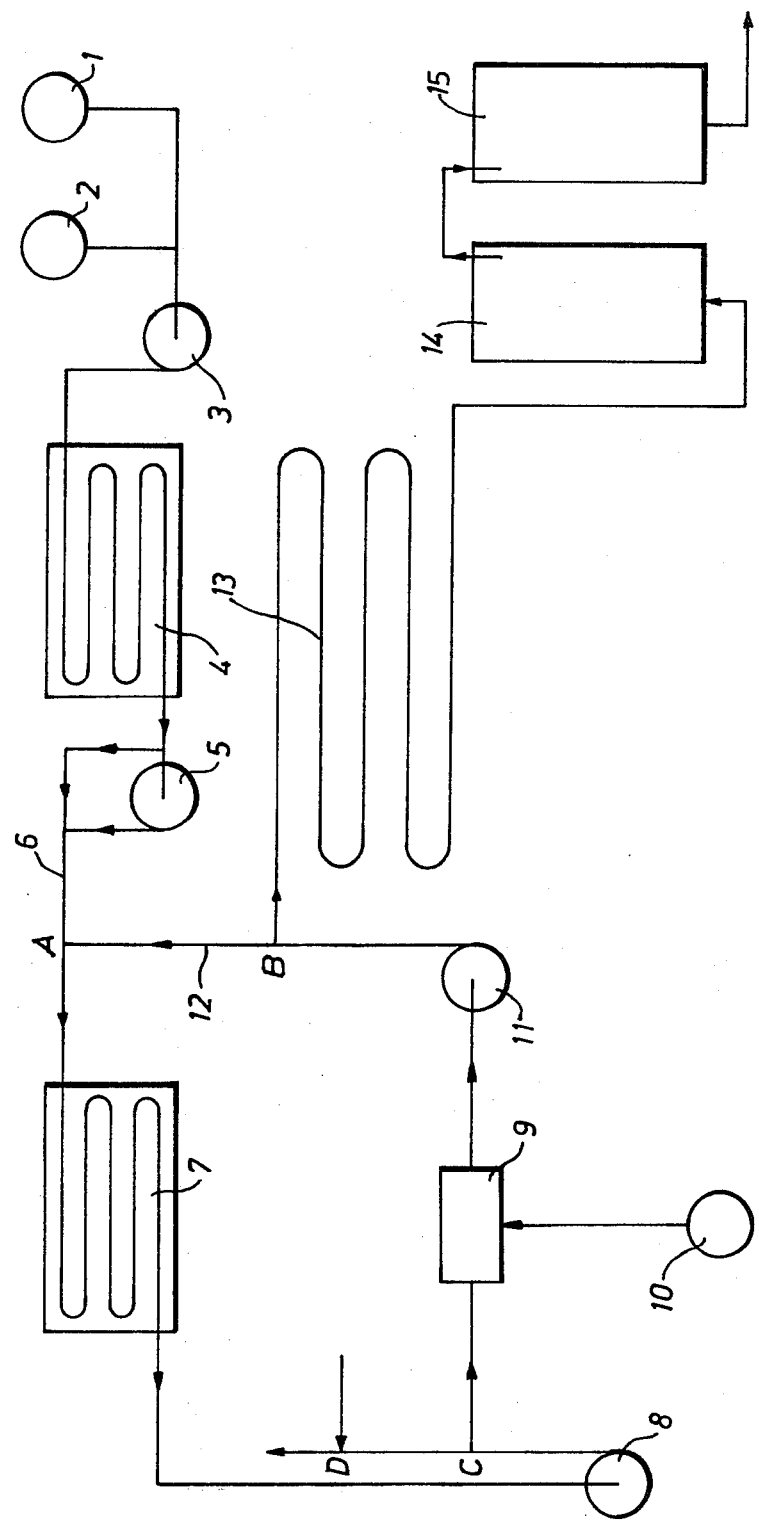

PROCESS FOR THE PRODUCTION OF AROMATIC POLYAMINES

This invention relates to a process for the continuous production of aromatic polyamines by condensing aromatic amines with formaldehyde in the presence of an acidic catalyst.

Aromatic polyamines or mixtures of aromatic polyamines corresponding to the formula:

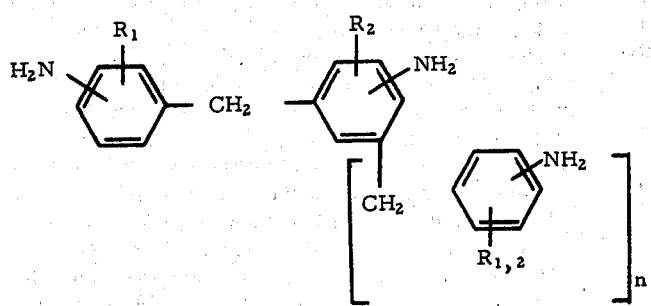

wherein $n$ is 0 or a positive integer and $R_1$ and $R_2$ are hydrogen, halogen or alkyl which, following phosgenation to the corresponding isocyanates, can be foamed with suitable polyols.

It is known that aromatic polyamines of the above type can be produced by batch condensation by introducing an aldehyde into an amine/acid mixture, subsequently completing the reaction at boiling temperature and then liberating the resulting polyamines by the addition of alkali, see for example, German patent specification No. 1,138,177. However, processes of this kind have the usual disadvantages of batch processes, such as inconsistent product quality, and unsatisfactory economy attributable to poor volume/time yields and plant unreliability, especially as regards the shut-off systems.

It is also known that aromatic polyamines can be continuously produced in special mixer units which, through high turbulence, guarantee rapid homogenization of the mixture of amine/catalyst with aldehyde, see for example, British patent specification No. 1,183,153. The disadvantage of this process is the deposition of polymeric precondensates in the heat exchangers whose efficiency is reduced as a result. Effective cooling of the mixture, which undergoes a rapid increase in temperature due to the highly exothermic reaction, is however necessary, in order to avoid the formation of undesirable secondary products consisting predominantly of polymeric secondary amines with a fibrous or reticular molecular structure (molecular weight in excess of 1,000). The intensive cooling required brings the associated disadvantage that intensive cooling promotes the aforementioned deposits in the reactor system, resulting in blockages.

Finally, it is known that fully reacted aldehyde/amine/catalyst mixtures can be recycled into the mixture of starting components at the beginning of the process, and passed again through the entire section of the plant in which the condensation reaction takes place, resulting in the formation of polyamine mixtures which are distinguished by their high solubility in organic solvents, see for example, German Offenlegungsschrift No. 1,959,168. Processes of this kind have the disadvantage that the products formed have a higher viscosity than those formed without recycling of the product, because some of the higher amines formed react with more aldehyde and monomeric amine to form polyamines having secondary amino groups, which can no longer be completely rearranged into primary amines. Unfortunately, amines of this kind when reacted with phosgene yield carbamic acid chlorides which corrode the phosgenation plants and, when foamed with polyols, produce foams having poor dimensional stability, especially in the cold.

It is therefore an object of this invention to provide a process for producing aromatic polyamines devoid of the foregoing disadvantages. It is another object of this invention to provide a process for producing aromatic polyamines by condensing a primary or secondary aromatic amine with formaldehyde or a formaldehyde precursor. A further object of this invention is to provide apparatus for the continuous production of aromatic polyamines. An additional object of this invention is to provide polyurethane foams using as the isocyanate precursor the phosgenation product of the aromatic polyamines prepared by the process of the invention.

The foregoing objects and others which will become apparent from the following description and the accompanying drawing, which schematically illustrates the process and apparatus of the invention are accomplished in accordance with the invention, generally speaking, by allowing the vigorous evolution of heat accompanying the reaction of aldehyde and catalyst/amine mixture to proceed simultaneously in spatially separate apparatus sections which are arranged in such a way that, in a cyclic system, a reaction mixture of low aldehyde content initially gives off the heat liberated in a heat exchanger, thereafter is condensed with the rest of the aldehyde until the ideal quantity is obtained, followed by the further evolution of heat, and finally, after the reaction has been continued in a heated residence vessel, the reaction mixture is worked up under alkaline conditions by methods well known to the art.

Accordingly, the present invention relates to a process for the production of aromatic polyamines comprising condensing a primary and/or secondary aromatic amine with formaldehyde in the presence of a suitable acid catalyst and liberating the resulting polyamines on completion of condensation by the addition of a basically reacting reagent, distinguished by the fact that the mixture containing amine, catalyst, aldehyde and precondensates formed therefrom, as well as water, issuing from a mixer at a maximum temperature of about 40°C., is divided into a. a side stream in which the heat liberated from the reacting mixture is dissipated in a heat exchanger following dilution with the total quantity of the mixture of amine and catalyst, cooled to below 40°C., required for the reaction, and the mixture thus obtained is re-introduced at a maximum temperature of 40°C. into the mixer where the optionally cooled aldehyde is added, and b. a main stream which is pumped, if desired, through a reaction zone kept at a maximum temperature of 40°C., into one or more heated residence reactors arranged in series in which the condensation reaction is completed at a temperature of from 80° to 200°C.

In the process according to the invention, the aromatic amine and the formaldehyde or formaldehyde-donor are used in quantities corresponding to a molar ratio of from about 10 : 1 to about 1 : 1, preferably from about 4 : 1 to about 2 : 1 based on monomeric formaldehyde. Acidic compounds preferably mineral acids, most preferably hydrochloric acid, are used as catalysts in the process according to the invention. In the process according to the invention, the molar ratio of amine to catalyst is from about 6 : 1 to about 1 : 1, preferably from about 3 : 1 to about 1 : 1.

Examples of aromatic amines suitable for use in the process according to the invention include aniline; o-, m-, and p-chloroaniline; o-, m-, and p-bromoaniline; o-, m-, and p-anisidine; o-, m-, and p-phenetidine; o-, m-, and p-toluidine; o-, m-, and p-ethylaniline; o-, m-, and p-isopropylaniline; o-, m-, and p-xylidines; a- and b-naphthylamine; o-, m-, and p-benzylaniline; o-, m-, and p-cyclohexylaniline; 2,4- and 2,6-diaminotoluene; o-, m-, and p-diaminobenzene; mixtures of the aforementioned amines; and mixtures of the aforementioned amines with their aldehyde condensation products. Aniline is preferably used.

In addition to these primary amines, it is also possible to use N-monosubstituted aryl amines, for example, N-($C_1$–$C_4$-alkyl)-substituted derivatives of the aforementioned primary aromatic amines, in the process according to the invention. Whereas primary polyphenyl polymethylene polyamines, which can be converted with phosgene into the corresponding polyisocyanates, are obtained when primary amines are used in the process according to the invention, corresponding N-substituted polyphenyl polymethylene polyamines, which are used inter alia for the production of ureas by reaction with isocyanates, are obtained when N-monosubstituted aromatic amines are used.

Finally, mixtures of primary and secondary aromatic amines can also be used in the process according to the invention, in which case the corresponding polyamines containing primary and secondary amino groups are obtained. Thus, for example, when a mixture of N-methylaniline and o-toluidine is used, a diamine of the following formula

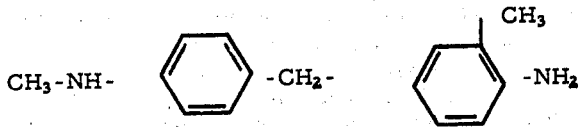

is formed in admixture with isomers, higher homologues and corresponding symmetrical compounds.

In addition to formaldehyde, preferably in aqueous or aqueous-alcoholic solution, it is also possible to use formaldehyde donors, such as methylal, in the process according to the invention.

As already explained, hydrochloric acid is preferably used as catalyst in the process according to the invention. Other acid compounds are also suitable, such as, for example, sulphuric acid, hydrobromic acid, gaseous hydrogen chloride, acetic acid, phosphorus oxychloride and the like.

With reference to the schematic diagram, the apparatus required for carrying out the process according to the invention comprises two supply vessels 1 and 2 for aromatic amine and catalyst, from which pipes lead to a common delivery pump 3 followed by a first condenser 4 from which a pipe 6 leads, optionally through another pump 5, through a mixing point A to a second condenser 7 whose output end is connected through another pump 8 to a mixer 9 which is in turn connected to a supply vessel 10 for formaldehyde. The output end of the mixer 9 is connected through the pump 11 to junction B which leads, on the one hand, through a pipe 12 to the mixing point A, and on the other hand through a pipe to a residence zone 13 and thence to reactors 14 and 15. Between the pump 8 and the mixer 9 there is a junction C from which a pipe leads via inlet D to two reactors (not shown) similar to 14 and 15.

The invention provides apparatus for carrying out the process according to the invention, which comprises separate supply vessels 1 and 2 for aromatic amine and catalyst from which pipes lead to a common delivery pump 3 followed by two condensers 4 and 7 arranged in series, a pipe 6 leading from the second condenser 7 to a mixer 9 which is connected to a supply vessel 10 for formaldehyde and whose output end is connected to a residence pipe opening into a reactor 13 distinguished by the fact that a return pipe 12 branches off between 9 and the residence zone 13, leading into the feed pipe 6 to the second condenser 7.

In the practical application of the process according to the invention, the temperature of the mixture of amine and catalyst leaving the condenser 4 is from about 5° to about 40°C., preferably from about 10° to about 25°C. After it has been combined with the side stream, the mixture flows through the condenser 7, leaving it at a temperature of from about 0° to about 40°C., preferably from about 10° to about 25°C. After the formaldehyde has been introduced into the mixer 9, the mixture is divided at junction B into a side stream delivered to the mixing point A and a main stream leading to the two reactors 14 and 15 via the residence zone 13. The quantitative ratio between side stream and main stream is from about 5 : 1 to about 1 : 3. The maximum temperature prevailing in the residence zone 13 is about 40°C. The temperature prevailing in the reactors 14 and 15 is from about 80° to about 200°C., preferably from about 95° to about 105°C.

The process according to the invention offers a convenient means of simultaneously producing two amine mixtures having differing viscosities. If a component stream is removed from the side stream between the condenser 7 and the mixer 9, more particularly between the pump 8 and the mixer 9 at junction C, and allowed to react to completion in heatable reactors similar to 14 and 15, after passage through a residence zone similar to 13, an amine mixture containing a large proportion of binuclear amines is obtained after working up under alkaline conditions due to the higher amine/formaldehyde ratio of the reaction mixture removed at C. In order to displace the isomer distribution in favour of 4,4'-diaminodiarylmethanes when aromatic monoamines are used, it is also of advantage additionally to feed in acidic catalyst at junction D in order to reduce the proportion of 2,4'-diaminodiarylmethanes.

The reaction product leaving the reactors 14 and 15 contains the end products partly in the form of their ammonium salts so that, for purification, the end products have to be subsequently subjected to working up under alkaline conditions in the customary manner.

To produce high-grade products, especially polyamines which can be reacted with phosgene to form the corresponding polyisocyanates without any residue formation, the temperature profile in particular is of crucial importance in the process according to the invention, in addition to an inert gas atmosphere (the apparatus components are preferably sealed off from the atmosphere and are under inert gas), and adequate turbulence of the reaction mixture, which can be adjusted with sufficiently high rates of products flow in the turbular reactor system or by means of a jet mixer. It has been found that a temperature of about 40°C. should not be exceeded in the pre-reaction section, i.e., before entry into the reactor 14. If temperatures higher than this are allowed in the pre-reaction section, deposits are formed on the walls of the reactor and phosgenation of the polyamine mixture is made difficult by resin-like deposits. At temperatures below 40°C. in the pre-reaction zone, the plant remains free from polymeric deposits and the polyamine mixture can be reacted with phosgene by known methods in the absence of any residue formation. Providing this critical temperature is observed, the reaction mixture flowing into the reactor 14 consists merely of the starting components and, predominantly, of N-substituted precondensates, while formation of the end products through reaction of the N-substituted precondensates by rearrangement into the corresponding nuclear-substituted end products, optionally accompanied by reaction with any excess of the starting amine, takes place solely in the reactor section 14 and 15. It has proved to be of advantage to heat the mixture leaving the pre-reaction zone immediately to about 80°C. or more on entry into the reactor 14 without any transition zone.

The process according to the invention affords the particular advantage that, because of the dilution effect due to recycling the side stream, the reaction mixture remains thinly liquid throughout. For this reason, the product can be cooled as required without causing any deposits on the heat-exchanger surfaces because it is impossible for a thixotropic phase to occur during the reaction in contrast to the continuous processes of the prior art. The heat exchanger 7 remains free from deposits even after a prolonged service period of several months.

By virtue of the principle according to the invention of recycling the side stream into the cooled amine/catalyst mixture and dissipating heat through the heat exchanger 7, and by suitably selecting the ratio of side stream to main stream, the reaction mixture does not exceed the critical temperature of about 40°C. anywhere before entering the reactors, for an average residence time of from about 30 seconds to about 15 minutes.

As already explained, it is possible by virtue of the process according to the invention to produce polyamines which are eminently suitable for the production of the corresponding polyisocyanates by simply phosgenating the polyamines in manners well known to the art.

Thus, the invention also relates to the use of the primary aromatic polyamines obtainable by the process according to the invention as a starting component in the production of polyisocyanates by the wellknown amine phosgenation process.

The invention is illustrated by the following Examples in which all parts and percentages are by weight unless otherwise indicated.

EXAMPLES

Example 1

A continuous stream of about 2 parts by volume of aniline from vessel 1 and 1 part by volume of about 30% aqueous hydrochloric acid from vessel 2 (molar ratio of aniline to hydrochloric acid about 2.32 : 1), is adjusted to about 15°C. in condenser 4 and introduced at point A into the loop (cyclic system). About 1 part by volume of formalin, in the form of about 30% aqueous solution, is introduced from the vessel 10 through the mixer 9 functioning on the principle of the water-jet pump (molar ratio of aniline to fromaldehyde, about 2 : 1). At junction B the product stream is divided into two equal parts, one half flowing through the reaction zone 13 to the reactors 14 and 15, while the other half is diluted at point A with freshly arriving aniline/aniline hydrochloride and, after passing through the condenser 7 re-enters the mixer. The temperatures are adjusted as follows: The aniline hydrochloride and formalin are adjusted to about 15°C. and the condenser 7 is operated in such a way that the temperature of the reacting mixture does not exceed about 25°C. at any point around the loop. At the end of zone 13, before entry into the reactor 14, the mixture has a temperature of about 40°C. After an average residence time of about 1 hour in the reactors 14 and 15 heated to from about 100° to about 120°C. (the conventional kettle reactors can be used as the reactors), the mixture is made alkaline with about 0.65 parts by volume of about 50% aqueous sodium hydroxide solution at a temperature of about 110°C., separated off from the aqueous/alkaline salt solution, and distilled in a column evaporator in vacuo at a temperature of from about 100° to about 230°C. until it is free from water and aniline. The polyamine mixture thus prepared has the following characteristics:

| | |
|---|---|
| Diphenyl methylene diamine content | 62% |
| Triphenyl dimethylene triamine content | 24% |
| Tetraphenyl trimethylene tetramine content | 10% |
| Pentaphenyl tetramethylene pentamine content | 5% |
| Viscosity at 80°C. | 63 cP |
| Yield, based on aniline used | 89% |

Example 2

The procedure as in Example 1 is followed except that the temperature in the loop between junction A and condenser 7 is allowed to rise to about 40°C., followed by cooling again at 7 to such an extent that the temperature at junction B is about 20°C. The polyamine mixture obtained has the following characteristics:

| | |
|---|---|
| Diphenyl methylene diamine content | 64% |
| Triphenyl dimethylene triamine content | 24% |
| Tetraphenyl trimethylene tetramine content | 9% |
| Pentaphenyl tetramethylene pentamine content | 4% |
| Viscosity at 80°C. | 61 cP |
| Yield, based on aniline used | 86% |

Example 3

The procedure is as in Example 2, except that the product stream is divided at junction B in such proportions that about 2 parts by volume flow through the loop while about 1 part by volume flows through zone 13. The polyamine mixture thus prepared has the following characteristics:

| | |
|---|---|
| Diphenyl methylene diamine content | 60% |
| Triphenyl dimethylene triamine content | 25% |
| Tetraphenyl trimethylene tetramine content | 10% |
| Pentaphenyl tetramethylene pentamine content | 5% |
| Viscosity at 80°C. | 66 cP |
| Yield, based on aniline used | 85% |

Example 4

The procedure is as in Example 2, except that instead of aniline the same volume of a mixture of about 90% of aniline and about 10% of 4,4'-diamino diphenyl methane is used as the amine. The polyamine mixture thus prepared has the following characteristics:

| | |
|---|---|
| Diphenyl methylene diamine content | 59% |
| Triphenyl dimethylene triamine content | 25% |
| Tetraphenyl trimethylene tetramine content | 10% |
| Pentaphenyl tetramethylene pentamine content | 6% |
| Viscosity at 80°C. | 72 cP |
| Yield, based on the amine mixture used | 93% |

Example 5

The procedure is as in Example 2, except that a mixture of about 10 parts by volume of aniline and about 5 parts by volume of about 30% hydrochloric acid is fed in at point A, while about 2 parts by volume of about 30% aqueous formalin solution is introduced into the mixer 9. The stream is divided at junction B in such proportions that about 5 parts by volume flow into the loop and about 3 parts by volume into the zone 13, while at junction C it is divided in a ratio of about 4 : 1, the larger component being delivered to mixer 9 while the smaller component is further treated in exactly the same way as the product flowing from B into the zone 13. The end product obtained from junction (B) has characteristics identical to those obtained in Example 2. The product branched off at C yields a polyamine mixture having the following characteristics:

| | |
|---|---|
| Diphenyl methylene diamine content | 84% |
| Triphenyl dimethylene triamine content | 12% |
| Tetraphenyl trimethylene tetramine content | 2% |
| Pentaphenyl tetramethylene pentamine content | 1% |
| Viscosity at 80°C. | 26 cP |

The total yield amounts to about 71%, based on the aniline used. The yield of low-viscosity product, based on aniline, amounts to about 48%, while the yield of higher-viscosity product amounts to about 86%, and the ratio of the corresponding product quantities amounts to about 1 : 2.7.

Example 6

The procedure is as in Example 2, except that instead of aniline the same volume of o-toluidine is used as the amine. The polyamine mixture thus prepared has the following characteristics:

| | |
|---|---|
| Di-(o-toluidyl)-methane content | 63% |
| Triamine content | 20% |
| Tetramine content | 5% |
| Yield, based on the o-toluidine used | 98% |

Example 7

The procedure is as in Example 2, except that a mixture of equal parts by volume of aniline and o-toluidine is used as the amine. The polyamine mixture thus prepared has the following characteristics:

| | |
|---|---|
| Diamino diphenyl methane content | 18% |
| Di-o-toluidyl methane content | 19% |
| Aminophenyl-o-toluidyl methane content | 37% |
| Triamine content | 23% |
| Tetramine content | 2% |
| Yield, based on the amine mixture used | 97% |

Example 8

The procedure is as in Example 2, except that N-methylaniline is used instead of aniline. The polyamine mixture obtained has the following characteristics:

| | |
|---|---|
| N,N'-dimethylamino diphenyl methane content | 54% |
| Triamine content | 25% |
| Tetramine content | 10% |
| Viscosity at 80°C. | 98 cP |
| Yield, based on the N-methylaniline used | 95% |

Example 9

The procedure is as in Example 2, except that a mixture of equal parts of N-methyl and N-ethyl aniline is used instead of aniline. The polyamine mixture obtained has the following characteristics:

| | |
|---|---|
| N,N'-dimethylamino diphenyl methane content | 11% |
| N,N'-diethylamino diphenyl methane content | 14% |
| N-methyl-N'-ethyl-diamino diphenyl methane content | 26% |
| Triamine content | 32% |
| Tetramine content | 15% |
| Viscosity at 80°C. | 133 cP |
| Yield, based on the amine mixture used | 90% |

Example 10

The procedure is as in Example 2, except that an equivalent volume of a mixture of equal parts by volume of o-toluidine and N-methylaniline is used instead of aniline. The polyamine mixture obtained has the following characteristics:

| | |
|---|---|
| Diamine content | 60% |
| Triamine content | 19% |
| Tetramine content | 7% |
| Viscosity at 80°C. | 97 cP |
| Yield, based on the amine mixture used | 96% |

Example 11

A solution of about 200 parts of the polyamine obtained in accordance with Example 1, in 1,300 parts by volume of chlorobenzene is allowed to flow, with cooling and stirring into a solution, cooled to about −10°C., of about 320 parts of phosgene in about 1,200 parts by volume of chlorobenzene. The rate of flow of the addition is adjusted in such a way that a temperature of about 30°C. is not exceeded. Finally, the mixture is slowly heated to about 100°C. while more gaseous phosgene is introduced, and the temperature of 100°C. is maintained for about 2 hours. The phosgene is removed by applying a water-jet vacuum, after which the solvent is distilled off in vacuo, leaving behind about 240 parts of a polyisocyanate mixture eminently suitable for the production of polyurethanes. Its content of binuclear, trinuclear, tetranuclear and pentanuclear components corresponds to that of the polyamine mixture used.

Although the invention is described in considerable detail in the foregoing Examples, it is to be understood that the Examples are intended solely for purposes of illustration and that many variations may be made by one skilled in the art without departing from the spirit and scope of the invention.

What is claimed is:

1. In a process for the production of an aromatic polyamine comprising condensing a primary or secondary aromatic amine with formaldehyde or a formaldehyde precursor in the presence of an acid catalyst and liberating the polyamine upon completion of condensation by the addition of a basically reacting reagent, wherein a first mixture of the total quantities of the amine and the catalyst required for the reaction is formed and cooled to below about 40°C. and wherein a second mixture containing amine, catalyst, aldehyde, precondensates formed therefrom, and water, issues from a mixer at a maximum temperature of about 40°C., the improvement which comprises separating said second mixture into
   a. a side stream which is admixed with the first mixture to form a reacting mixture liberating heat, which heat is dissipated in a heat exchanger, and introducing the reacting mixture at a temperature of at most about 40°C. into the mixer into which the formaldehyde or formaldehyde precursor is added, and
   b. a main stream which is passed through a reaction zone, maintained at a maximum temperature of about 40°C., and into a heated residence reactor maintained at a temperature from about 80°C. to about 200°C., wherein the condensation reaction is completed.

2. The process of claim 1, wherein the ratio of side stream to a main stream is from about 5 : 1 to about 1 : 3.

3. The process of claim 1, wherein a second side stream is removed from the system immediately before the mixer, and is reacted, in heated residence reactors to form a polyamine with a binuclear polyamine content of more than 70% by weight.

4. The process of claim 1 wherein aniline, o-toluidine, N-methylaniline, N-ethylaniline or a mixture thereof, is used as the aromatic amine.

5. The process of claim 1, wherein hydrochloric acid is used as the catalyst.

* * * * *